United States Patent

Tsuji

[11] 4,267,377
[45] May 12, 1981

[54] INTERMEDIATES FOR STEROID SYNTHESIS

[75] Inventor: Jiro Tsuji, Kamakura, Japan

[73] Assignee: Takeda Chemical Industries, Ltd., Osaka, Japan

[21] Appl. No.: 71,405

[22] Filed: Aug. 30, 1979

[30] Foreign Application Priority Data

Sep. 8, 1978 [JP] Japan .................. 53-111092

[51] Int. Cl.³ .................. C07C 49/633; C07C 49/637
[52] U.S. Cl. .................. 568/374; 260/345.9 R; 560/256
[58] Field of Search ........ 260/586 F, 586 E, 345.9 R; 568/374; 560/256

[56] References Cited

U.S. PATENT DOCUMENTS 3,816,536  6/1974  Eder et al. .................. 260/586 F

OTHER PUBLICATIONS

Houdewind, P. et al., *Tetrahedron Letters*, No. 27, pp. 2359-2362, (1974).

*Primary Examiner*—Natalie Trousof
*Assistant Examiner*—L. Hendriksen
*Attorney, Agent, or Firm*—Craig & Antonelli

[57] ABSTRACT

A compound of the general formula:

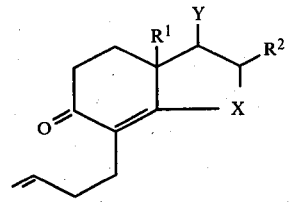

wherein $R^1$ is a lower alkyl group; $R^2$ is H or a lower alkyl group; Y is an oxo group, H or an unprotected or protected hydroxyl group; X is a methylene or ethylene group, for example, 7,7a-dihydro-7aS-methyl-4-(3-butenyl)-1-tert. butoxy-5(6H)-indanone, which is an intermediate for steroids, is prepared by dehydrative cyclization of a compound of the general formula of

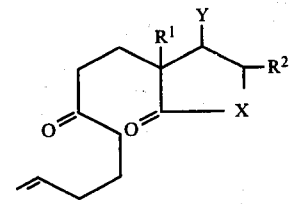

wherein $R^1$, $R^2$, X and Y are the same as above.

3 Claims, No Drawings

INTERMEDIATES FOR STEROID SYNTHESIS

This invention relates to intermediates for steroid and a method for producing same.

Steroids are not only isolated from natural materials but also methods of total synthesis thereof have been developed in recent years. In particular, methods via the following structure (I) are gathering attention. [Doklady Akademii Nauk S.S.S.R. 171 880 (1966)]

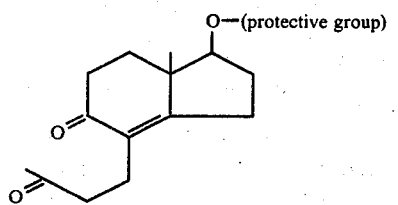

However, synthesis of this intermediate (I) requires a large number of steps, involves the use of expensive starting materials or includes reactions which give only poor yield.

The present inventor carried out an intensive research under the circumstances and discovered that a compound of general formula (VI) can be produced by the following procedure. 1,7-Octadien-3-one (II), which can be easily obtained from butadiene, is allowed to react with a compound of the general formula (III) to obtain a compound of the general formula (IV), which is then dehydratively cyclized to a compound of the general formula (V). The oxo group of this compound (V) is selectively reduced, if necessary and, furthermore, the resultant hydroxyl group is protected, if necessary. Thereafter, the terminal olefin is oxidized to methyl ketone in an oxygen-containing atmosphere in the presence of a small amount of water and a palladium catalyst with a reoxidizing agent. The above series of reaction steps yields the compound (VI).

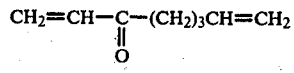

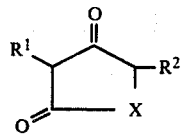

(wherein $R^1$ is a lower alkyl group; $R^2$ is H or a lower alkyl group; X is a methylene or ethylene group)

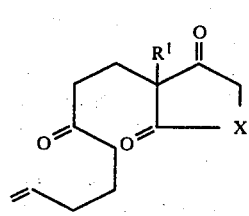

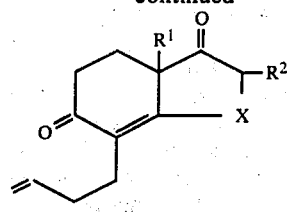

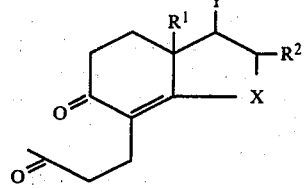

(wherein Y is an oxo group, H or an unprotected or protected hydroxyl group and the other symbols of $R^1$, $R^2$ and X are the same as defined above)

This invention is therefore concerned with:
(1) a compound of the general formula (V);
(2) a method of producing a compound of the general formula (V) wherein a compound of the general formula (IV) is dehydratively cyclized; and
(3) a method of producing a compound of the general formula (VI) wherein a compound of general formula (V) is oxidized in an oxygen-containing atmosphere in the presence of a small amount of water and a palladium catalyst with a reoxydizing agent.

Referring to the above general formulas, the lower alkyls $R^1$ and $R^2$ each means an alkyl of 1 to 3 carbon atoms. The protective group on protected hydroxyl Y may be any appropriate group, as long as it can be removed under mild conditions, e.g. under acidic conditions established by hydrochloric acid, sulfuric acid or the like or by catalytic reduction. Thus, for example, tert-butyl, tetrahydropyranyl, benzyl, acetyl, etc. may be mentioned. When Y is a ketone, the protective group may for example be 1,3-dioxolane.

Compounds having the general formula (V) include:
(1) 7,7a-dihydro-7aS-methyl-4-(3-butenyl)-1-tert-butoxy-5(6H)-indanone;
(2) 7,7a-Dihydro-2-methyl-7aS-methyl-4-(3-butenyl)-1-tert-butoxy-5(6H)-indanone;
(3) (±) 7,7a-Dihydro-7aS-ethyl-4-(3-butenyl)-1,5(6H)-indandione;
(4) (±) 7,7a-Dihydro-2-ethyl-7aS-methyl-4-(3-butenyl)-1-hydroxy-5(6)-indanone;
(5) (±) 7,7a-Dihydro-7aS-isopropyl-4-(3-butenyl)-1-hydroxy-5(6H)-indanone;
(6) (±) 7,7a-Dihydro-7aS-methyl-4-(3-butenyl)-1,5(6H)-indandione;
(7) (±) 7,7a-Dihydro-7aS-methyl-4-(3-butenyl)-1-hydroxy-5(6H)-indanone;
(8) 3,4,8,8a-Tetrahydro-5-(3-butenyl)-8aS-methyl-1,6-(2H,7H)-naphthalenedione;
(9) 5-t-Butoxy-4aβ-methyl-1-(3-butenyl)-2,3,4,4a,5,6,7,8-octahydronaphthalen-2-one;
(10) 3,4,8,8a-Tetrahydro-5-(3-butenyl)-8aS-ethyl-1,6-(2H,7H)-naphthalenedione.

The 1,7-octadien-3one (II) can be produced in the following manner. Butadiene is dimerized in the presence of acetic acid to obtain 3-acetoxy-1,7-diene, which is then hydrolyzed to 1,7-octadien-3-ol (Tetrahedron Letters 1967, 2451). This 1,7-octadien-3-ol is oxidized with an oxidizing agent such as chromic anhydride, chromic anhydride-pyridine complex, 2,3-dichloro-5,6-dicyano-1,4-benzoquinone (DDQ), manganese dioxide, silver carbonate, copper oxide or the like.

The cyclopentanedione derivative of general formula (III) can be produced, for example by the procedures described in Journal of the American Chemical Society 65, 562 (1943), Journal of Organic Chemistry 32, 1236 (1967), Bulletin de la Societe Chimique de France, 1955, 1036, etc.

The condensation reaction between the compounds (II) and (III) is preferably conducted in the presence of a basic compound such as sodium hydride, triethylamine, tributylamine, sodium hydroxide or pyridine. This reaction is desirably carried out in an inert solvent such as benzene, ethyl acetate, ethanol, methanol, tetrahydrofuran, dimethylformamide, dimethoxyethane or dioxane. Although the reaction proceeds satisfactorily at lower temperatures then room temperature, such as from aboout 0° C. to 10° C., it may be carried out at higher or lower temperatures.

The compound (IV) thus obtained is preferably subjected to selective reduction, whereby the oxo group on the cyclopentane ring is reduced so that $R^1$ will be $\beta$-oriented for the next cyclization reaction. This selective reduction is carried by subjecting the compound (IV) to an action of a microorganism capable of reducing the compound (IV) to a compound of the formula (IV') wherein $R^1$ is $\beta$-oriented, or a culture broth of the same microorganism.

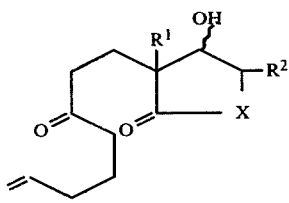

The above-mentioned microorganism includes microorganisms belonging to the genera Candida, Debaryomyces, Pichia, Schizosaccharomyces, Petasospora, Hansenula, Torulopsis, Saccharomycodes, etc. Useful species are *Candida solani, Candia robusta, Candida krusei, Candida utilis, Candida fabianii, Candida tenuis, Candida scottii, Debaryomyces nicotianae, Debaryomyces vini, Debaryomyces vanriji, Debaromyces globosus, Debaryomyces phaffii, Pichia wickerhamii, Pichia etchellsii, Pichia pijperi, Pichia quercuum, Petasospora chambardi, Saccharomycodes ludwigii, Torulopsis aeria, Torulopsis colliculosa, Torulopsis candida, Torulopsis globosa, Torulopsis vinacea, Torulopsis pseudaeria, Hansenula wingei, Hansenula holstii, Hansenula beijerinckii, Hansenula capsulata* and *Hansenula saturnus.*

The starting compound (IV) is allowed to react with such a microorganism or a culture broth of the microorganism to obtain the desired compound (IV'). The culture broth means the broth containing the microbial cells, milled cells, or an enzyme system available on extraction thereof, for instance. For example, after the microorganism is cultivated in the routine manner and the microbial cells are separated or not from the resultant broth, the starting compound is contacted with the broth or cells. It is also possible to simultaneously effect both cultivation of the microorganism and reduction of the starting compound by growing the microorganism in a culture medium containing the starting compound.

A nutrient medium suitable for growth of the microorganism may contain assimilable carbon sources and nitrogen sources and inorganic salts, vitamins, amino acids, etc. which are necessary for growth. The carbon sources may include glucose, sucrose, dextrin, starch, glycerin, etc. The nitrogen sources include organic nitrogen-containing materials, e.g. peptone, meat extract, casein, Edamine, corn steep liquor, yeast, yeast extract, and inorganic nitrogen-containing materials, e.g. ammonium nitrate, ammonium phosphate, ammonium sulfate, sodium nitrate, etc. The inorganic salts may be potassium phosphate, sodium chloride, magnesium sulfate, etc. Such nutrients are used in appropriate proportions to prepare a culture medium.

The microorganism can be cultivated by any of stationary, shaking or aerobic submerged cultural methods with shaking. The starting compound (IV) can be added at any time in a period of cultivation, i.e., in the beginning or thereafter. The material compound (IV) is added in fine powders or after dissolved or suspended in a suitable solvent such as acetone, methanol, ethanol, ethylene glycol, propylene glycol, dimethylformamide or dioxane with or without a surfactant and/or a dispersing agent. The addition may be made at one time or continuously or intermittently over a certain period of time.

Alternatively, after microbial cells obtained by the cultivation or a reducing enzyme system which plays a role in the reducing reaction is separated from the culture broth or cells, they are suspended or dissolved in water or a buffer solution having an appropriate pH or ionic strength. The starting material and a hydrogen donor are contacted with the solution or suspension to reduce the starting material.

Acidity, temperature, reaction period of time and other conditions of the reaction for reduction of the compound (IV) are variable depending upon the compound (IV) and microorganism employed. The most preferred conditions should be selected in each instance.

The compound (IV') thus produced and accumulated can be recovered by various procedures. For example, the contemplated substance is adsorbed on a suitable adsorbent (alumina, activated carbon, etc.) and, then desorbed with an appropriate solvent (e.g. methanol, ethanol, etc.). Alternatively, the same is directly extracted with an organic solvent capable of forming two distinct phases with water, such as a halogenated hydrocarbon e.g. chloroform, methylene chloride, ethylene chloride, etc., an acetic acid ester or the like. One of the other ways is a counter-current distribution procedure where difference in distribution ratios between two liquids is utilized. Chromatographic separation methods using a suitable carrier e.g. alumina, silica gel, cellulose pulp, etc. or procedures utilizing solubility differences may also be employed. These methods can be selectively employed. The resultant compound (IV') may then be protected, if necessary, with the afore-mentioned protective group in the routine manner.

The cyclization reaction of compound (IV) or (IV') proceeds readily in the presence of a weakly basic compound such as $\beta$-alanine, proline or phenylalanine, preferably L-form of the latter two compounds. The presence of a small amount of strong acid, e.g. perchloric acid, leads to satisfactory results. The reaction is preferably conducted in a solvent such as water, methanol, ethanol, propanol, acetonitrile, methylene chloride, benzene or tetrahydrofuren. The reaction may be conducted at room temperature or an elevated temperature (e.g. under reflux).

The oxidation reaction of compound (V) can be conducted in an oxygen-containing atmosphere, e.g. air, in the presence of a small amount of water and a palladium catalyst such as palladium chloride with a reoxidizing agent such as a copper compound, e.g. cuprous chloride, cupric chloride, cupric nitrate, etc., an iron compound, e.g., ferric chloride and benzoquinone. This reaction may be conducted in the presence of an inert solvent such as dimethylformamide, methanol, ethanol, propanol, sulfolane, dimethoxyethane, dioxane or the like. Although the reaction proceeds satisfactorily at room temperature, it may be conducted at higher or lower temperature if necessary. The reaction is conducted in the presence of oxygen at atmospheric or supratmospheric pressure, preferably with stirring or shaking.

The compound (VI) is of great use as an intermediate for the synthesis of various steroids.

The resulting compound (VI) can further be transformed by the method described in Angewandte Chemie 72 (1960), 725–730, ibid 108 (1975), 2673–2679 for instance, into 19-nor-testosterone steroids, estrone steroids, 9,11-dehydro-testosterone steroids, androsterone steroids, cortisone steroids, etc.

REFERENCE EXAMPLE

In 100 cc of carbon tetrachloride is dissolved 3.1 g of 1,7-octadien-3-ol, followed by addition of 10 g of active manganese dioxide. The mixture is stirred at room temperature for 4 days. The reaction mixture is filtered and the solvent is distilled off under a reduced pressure of 20–30 mm Hg. As a fraction at 30°–32° C./4 mm Hg, there is obtained 2 g of 1,7-octadien-3-one. The above fraction is identified to be 1,7-octadien-3-one by the following analyses.

Infrared spectrometry: 1695 cm$^{-1}$, 1680 cm$^{-1}$, 1640 cm$^{-1}$, 910 cm$^{-1}$.

NMR (CCl$_4$) spectroanalysis: δ 0.9–1.8(4H, methylene), 2.49(2H, triplet, —CH$_2$—CO), 4.7-6.3(6H, olefin).

EXAMPLE 1

(1) 2-Methyl-2-(3-oxo-7-octenyl)-1,3-cyclohexanedione 1,7-Octadien-3-one(0.24 g), 2-methyl-1,3-cyclohexanedione(0.5 g) and triethylamine (1 ml) are added to ethyl acetate (10 ml), and the mixture is stirred at room temperature for 24 hours. The triethylamine and acetic acid are evaporated off and the residue is purified by silica gel column chromatography(methylene chloride) to recover 0.39 g of the above-indicated compound. [IR 1700–1730 cm$^{-1}$, 920 cm$^{-1}$; NMR 1.10 ppm(3H, singlet, —CH$_3$), 4.6–6.0 ppm(3H, multiplet, vinyl)].

(2) 3,4,8,8a-tetrahydro-5-(3-butenyl)-8a-methyl-1,6-(2H,7H)-naphthalenedione

The triketone obtained in (1) (2.732 g), β-alanine (3.6 g) and 1N-perchloric acid (16 ml) are added to acetonitrile (100 ml) and the mixture is refluxed for 7 days. After cooling to room temperature, water is added and the organic layer is extracted with methylene chloride. The extract is washed with water and an aqueous sodium chloride solution, dried over magnesium sulfate and filtered. The solvent is removed. The residue is purified by silica gel column chromatography to recover 1.838 g of the above-indicated compound. [IR 1715 cm$^{-1}$, 1665 cm$^{-1}$, 920 cm$^{-1}$, NMR 1.31 ppm (3H, singlet, CH$_3$), 4.6–6.1(3H, multiplet, vinyl)].

(3) 3,4,8,8 a-tetrahydro-5-(3-oxobutyl)-8a-methyl-1,6-(2H,7H)-naphthalenedione

Palladium chloride (0.18 g), cuprous chloride (1.0 g) and water (2 ml) are added to dimethylformamide (20 ml) and the mixture is stirred in an oxygen-containing atmosphere at room temperature for 2 hours. The olefin obtained in (2) (1.761 g) is added to the above solution and stirred in an oxygen-containing atmosphere for 24 hours. Following addition of dilute hydrochloric acid, the organic layer is extracted with ether, washed with water and an aqueous sodium chloride solution in that order, dried over magnesium sulfate and filtered. The solvent is then evaporated off and the residue is purified by silica gel column chromatography (hexane:ether=3:1) to recover 1.404 g of the above-indicated compound. [IR 1710 cm$^{-1}$, 1663 cm$^{-1}$; NMR 1.40 pp, (3H, singlet, —CH$_3$), 2.10 ppm (3H, singlet COCH$_3$)].

EXAMPLE 2

(1) 2-Methyl-2-(3-oxo-7-octenyl)-1,3-cyclopentanedione 1,7-Octadien-3-one(1.782 g), 2-methyl-1,3-cyclopentanedione (2 g) and triethylamine (4 ml) are added to ethyl acetate (40 ml) and the mixture is stirred at room temperature for 30 hours. The triethylamine and ethyl acetate are evaporated off and the residue is purified by silica gel column chromatography (methylene chloride) to recover 2.744 g of the above-indicated compound. [IR 1723 cm$^{-1}$, 1641 cm$^{-1}$, 918 cm$^{-1}$; NMR 1.02 ppm (3H, singlet, —CH$_3$), 4.7-6.2 (3H, multiplet, vinyl)].

(2) (±) 7,7a-Dihydro-7a-methyl-4-(3-butenyl)-1,5(6H)-indandione

The triketone obtained in (1) (2.744 g), β-alanine (2.2 g) and 1 N perchloric acid (5 ml) are added to acetonitrile (50 ml) and the mixture is refluxed for 5 days. After cooling to room temperature, water is added and the organic layer is extracted with methylene chloride, washed with water and an aqueous sodium chloride solution, dried over magnesium sulfate and filtered. The solvent is then removed and the residue is purified by silica gel column chromatography (methylene chloride). By the above procedure is obtained 1.838 g of the above-indicated compound. [IR 1745 cm$^{-1}$, 1662 cm$^{-1}$, 911 cm$^{-1}$; NMR 1.25 ppm(3H, singlet, CH$_3$), 4.7-6.1(3H, multiplet, vinyl)]

(3) (±) 7,7a-dihydro-7a-methyl-4-(3-oxobutyl)-1,5(6H)-indandione

Palladium chloride (100 mg), cuprous chloride (500 mg) and water (5 ml) are added to dimethylformamide (50 ml) and the mixture is stirred in an oxygen-containing atmosphere at room temperature for 2 hours. The olefin obtained in (2) (723 mg) is added to the above solution and the mixture is stirred in an oxygen-containing atmosphere for 5 hours. After dilute hydrochloric acid is added, the organic layer is extracted with ether and the extract is washed with water and an aqueous sodium chloride solution in that order, dried over magnesium sulfate and filtered. The solvent is then removed and the residue is purified by silica gel column chromatography (ether:hexane=1:3). By the above procedure is obtained 588 mg of the above-indicated compound (solid). [IR 1745 cm$^{-1}$, 1715 cm$^{-1}$, 1665 cm$^{-1}$; NMR 1.25 ppm(3H, singlet, CH$_3$), 2.02(3H, singlet, COCH$_3$)].

EXAMPLE 3

(1) 2-Methyl-2-(3-oxo-7-octenyl)-1,3-cyclopentanedione obtained in Example 2 (1) (3.0 g), phenylalanine (l-form, 2.5 g) and 1 N perchloric acid solution (5 ml)

are added to acetonitrile (100 ml) and heated under reflux for 4 days. After the reaction mixture is cooled to room temperature and almost all phenylalanine precipitated is filtered, water is added and an organic layer is extracted with ethylene chloride. The extracted material is washed with water and an aqueous sodium chloride solution before drying over magnesium sulfate. The solvent is distilled off after filtration. Purification is made with silica gel column chromatography (hexane:ether=3:1) to obtain (+) 7,7a-dihydro-7aS-methyl-4-(3-butenyl)-1,5(6H)-indandione (2.38 g). $[\alpha]_D^{20} = 214°$ (chlorform).

(2) Palladium chloride (177 mg), cuprous chloride (990 mg) and water (1 ml) are added to dimethylformamide (15 ml) and the mixture is stirred in an oxygen-containing atmosphere at room temperature for 2 hours. To the solution is added the olefin (2.38 g) obtained in (1) and the mixture is stirred in an oxygen-containing atmosphere for 12 hours. After dilute hydrochloric acid is added, the organic layer is extracted with ether. The extract is washed with water and an aqueous sodium chloride solution, dried over magnesium sulfate and filtered. The solvent is distilled off and the residue is purified by silica gel column chromatography (ether:hexane=1:3), to obtain (+) 7,7a-dihydro-7aS-methyl-4-(3-oxobutyl)=1,5(6H)-indandione (2.0 g).

$[\alpha]_D^{23} = 184°$ (74% EE) When recrystallization is made in ether, $\alpha$ value is: $[\alpha]_D^{23} = +254.6°$ (C=1.235, Benzene) (same as disclosed in literature).

m.p.: 72°–73° C.

NMR (CCl4) δ value (ppm): 1.23(3H,s,angular methyl), 2.03(3H,s,terminal methyl).

IR (KBr): 1650, 1710, 1740 cm$^{-1}$.

(3) To a solution of triketone (1.0142 g) obtained from (2) in dry methanol (10 ml) are added methyl orthoformate (0.924 ml) and a 0.5 wt.% solution of p-toluene sulfonic acid (0.5 ml) in methanol and stirred at room temperature for 15 minutes. The reaction solution is passed through silica gel column and removed the solvent to obtain a crude (+) 7,7a-dihydro-7aS-methyl-4-(3,3-dimethoxybutyl)-1,5(6H)-indandione.

NMR (benzene, external standard, trimethylsilane) δ value (ppm): 0.48(3H,s,angular methyl), 0.88(3H,s,terminal methyl), 2.68(6H,s,—OCH3).

IR: 1660 cm$^{-1}$, 1750 cm$^{-1}$.

(4) The ketalized compound (1.32 g) obtained in (3) is dissolved in dry benzene and heated to a temperature of boiling point of benzene. To the solution is added malonic acid (5 mg). About ⅔ solvent in volume is removed over about 20 minutes by distillation. After the reaction, the solution is lowered to a room temperature. The solution is made alkaline by adding an aqueous saturated sodium bicarbonate solution and extracted with benzene. The extracted solution is washed with an aqueous saturated sodium chloride solution, and dried over MgSO4. The solvent is distilled off from the solution to obtain a crude product of (−)3-methoxy-3,6aS-dimethyl-1,2,3,5,6,6a,7,8-octahydrocyclopenta[f][1]benzopyran-7-one (1.16 g).

NMR (CCl4) δ value (ppm); 1.08(3H, s,angular methyl), 1.38 (3H,s,terminal methyl), 3.20(3H,s,—OCH3), 5.42(1H,m,

IR: 1740 cm$^{-1}$, 1640 cm$^{-1}$.

(5) The crude product (1.16 g) obtained in (4) is dissolved in dry tetrahydrofuran (20 ml) and ice-cooled. To a solution in which ¾ molar equivalent of LiAlH4 is suspended in dry tetrahydrofuran (10 ml) and ice-cooled, is added the above solution dropwise under stirring. After the completion of the dropwise addition, the solution is left to stand for 15 minutes. To the solution are added slowly water (0.15 ml), a 15% aqueous NaOH solution (0.15 ml) and water (0.45 ml) in this order under ice-cooling. After the reaction is over, the solid is filtered and extracted with ether. The solution is dried over MgSO4 and the solvent is distilled off, thereby to obtain a crude product of (−)3-methoxy-3,6a-dimethyl-1,2,3,5,6,6a,7,8-octahydrocyclopenta [f][1] benzopyran-7β-ol (1.01 g).

NMR (benzene) δ value (ppm): 1.20(3H,s,angular methyl), 1.40(3H,s,terminal methyl), 3.20 and 3.22(3H,2s,—OCH3), 5.18(1H,m,

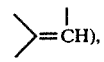

4.08(1H,t,

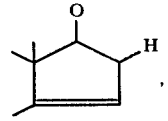

J=8 Hz).

IR: 3400 cm$^{-1}$, 1640 cm$^{-1}$.

(6) To a solution of the crude product (1.01 g) obtained from (5) in ethyl acetate (20 ml) is added 5% Pd/C and stirred at room temperature under one atmospheric pressure of H2 for 1.5 hours. After the reaction, Pd/C is removed with celite and the solvent is distilled off from the solution to obtain a crude product (−)3-methoxy-3,6a-dimethyl-1,2,3,5,6,6aS,7,8,9,9aα-deca-hydrocyclopenta[f][1]benzopyran-7β-ol(0.97 g).

NMR (benzene), δ value (ppm): 0.90 and 0.95 (3H,2s,angular methyl), 1.38 (3H,s,terminal methyl), 3.26 and 3.22 (3H,2s,—OCH3).

IR: 3420 cm$^{-1}$, 1680 cm$^{-1}$.

(7) The crude product (0.97 g) obtained from (6) is dissolved in ethanol (20 ml). To the solution is added a 3 N hydrochloric acid solution (5 ml) and stirred for 5 minutes. After a 6 N aqueous sodium hydroxide solution (20 ml) is added to the solution and heated at 80° C. for 15 minutes, the solution is controlled to pH of 4–5 by 1 N-sulfuric acid before the solvent is distilled under reduced pressure. The residue is dissolved in methylene chloride (60 ml), washed with water and purified with silica gel column chromatography to obtain (−)Des-A-17β-hydroxy-9-estren-5-one (460 mg). Yield: ((3) through (7)) 50%.

$[\alpha]_D^{23} = -45.6$ (C=1,CHCl3).

m.p.: 113° C.

NMR (CDCl3) δ value (ppm): 0.92 (3H,s,angular methyl), 3.78 (2H,m,—OH), 5.87(1H,m,enone).

IR: 3400 cm$^{-1}$, 1650 cm$^{-1}$.

I claim:

1. A compound of the general formula:

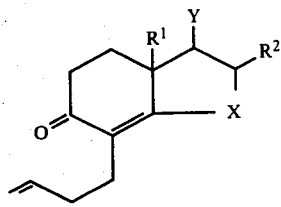

wherein R¹ is a lower alkyl group containing from 1 to 3 carbon atoms; R² is H or a lower aklyl group containing from 1 to 3 carbon atoms; Y is an oxo group, H or an unprotected or protected hydroxyl group, the protective group on the protected hydroxyl being a group that may be removed under acidic condition or catalytic reduction; and X is a methylene or ethylene group.

2. 3,4,8,8a-Tetrahydro-5-(3-butenyl)-8aS-methyl-1,6-(2H,7H)-naphthalenedione.

3. 7,7a-Dihydro-7aS-methyl-4-(3-butenyl)-1,5 (6H)-indandione.

* * * * *